United States Patent [19]

Quaranta et al.

[11] Patent Number: 5,658,789
[45] Date of Patent: Aug. 19, 1997

[54] PROMOTION OF EPITHELIAL CELL ADHESION AND HEMIDESMOSOME ASSEMBLY BY A LAMININ-LIKE MOLECULE

[75] Inventors: Vito Quaranta, La Jolla, Calif.; Marketta Hormia, Helsinki, Finland

[73] Assignee: Desmos, Inc., San Diego, Calif.

[21] Appl. No.: 445,135

[22] Filed: May 19, 1995

Related U.S. Application Data

[63] Continuation-in-part of Ser. No. 151,134, Nov. 12, 1993, Pat. No. 5,422,264.

[51] Int. Cl.$^6$ .............................. C12N 5/00; C12N 5/08; C07K 14/00
[52] U.S. Cl. ........................ 435/375; 435/325; 514/2; 530/350; 530/827; 530/828; 530/834
[58] Field of Search .......................... 435/240.1, 240.2; 514/2; 530/350, 827, 828, 834

[56] References Cited

U.S. PATENT DOCUMENTS

| | | | |
|---|---|---|---|
| 5,273,900 | 12/1993 | Boyce | 435/240.23 |
| 5,422,264 | 6/1995 | Quaranta et al. | 435/240.2 |
| 5,541,106 | 7/1996 | Jones | 435/204.243 |

FOREIGN PATENT DOCUMENTS

| | | |
|---|---|---|
| WO8903392 | 4/1989 | WIPO. |
| WO9217498 | 10/1992 | WIPO. |
| WO9405316 | 3/1994 | WIPO. |
| WO9506660 | 3/1995 | WIPO. |

OTHER PUBLICATIONS

Green, K.I. et al., J. Cell. Biol. vol. 109(#4, pt. 2), p. 46A, abstract #241. 1989.

Thiery, J.P. et al., Cell Biology International, vol. 15(#5), p. 365, abstract #S5–4. 1994.

Boukamp, et al., "Normal Keratinization in a Spontaneously Immortalized Aneuploid Human Keratinocyte Cell Line", *The Journal of Cell Biology*, 106: 761–771, 1988 Mar.

Chapman, et al., "Abnormal Expression of Hemidesmosome–like Structures by Junctional Epidermolysis Bullosa Keratinocytes in Vitro", *British Journal of Dermatology*, 123:137–144, 1990.

Garrison, et al., "Drosophila Laminin a Chain Sequence, Interspecies Comparison, and Domain Structure of a Major Carboxyl Portion", *The Journal of Biological Chemistry*, 266:34:22899–22904, 1991.

Giudice, et al., "Identification of Two Collagen Domains within the Bullous Pemphigoid Autoantigen, BP180", *J. Clin. Invest.*, 87:734–738, 1991.

Hieda, et al., "Identification of a New Hemidesmosomal Protein, HD1: A Major, High Molecular Mass Component of Isolated Hemidesmosomes", *The Journal of Cell Biology*, 116:6:1497–1506, 1992.

Hopkinson, et al., "Cytoplasmic Domain of the 180–kD Bullous Pemphigoid Antigen, A Hemidesmosomal Component: Molecular and Cell Biologic Characterization", *The Journal of Investigative Dermatology*, 99:3:264–270, 1992.

Hormia, et al., "The Distribution of Integrin $\alpha_6\beta_4$ in Keratinocytes is Modulated by Rat Carcinoma Cells", *Meeting of the International Association For Dental Research, Chicago, IL*, 1993.

Izumi, et al., "In Vitro Induction of Ornithine Decarboxylase in Urinary Bladder Carcinoma Cells", *Cancer Research*, 41:405–409, 1981.

Jones, et al., "$\alpha_6\beta_4$ Integrins: Their Role in the Assembly of the Hemidesmosome (HD) and in Signal Transduction", *J. Cellular Biochem.*, 16F:142, 1992.

Jones, et al., "Intermediate Filament–Plasma Membrane Interactions", *Cell Biology*, 3:127–132, 1991.

Kallunki, et al., "A Truncated Laminin Chain Homologous to the B2 Chain: Structure, Spatial Expression, and Chromosomal Assignment", *The Journal of Cell Biology*, 119:3:679–693, 1992.

Klatte, et al., "Immunochemical Characterization of Three Components of the Hemidesmosome and Their Expression in Cultured Epithelial Cells", *The Journal of Cell Biology*, 109:6:Pt.2:3377–3390, 1989.

Kurpakus, et al., "Surface Relocation of $Alpha_6Beta_4$ Integrins and Assembly of Hemidesmosomes in an in Vitro Model of Wound Healing", *The Journal of Cell Biology*, 115:(6):1737–1750, 1991.

Kurpakus, et al., "Integrins in the Hemidesmosome", *J. Cell Biol.*, 111:(5.Pt.2), 1990.

Langhofer, et al., "The Matrix Secreted by 804G Cells Contains Laminin–Related Components that Participate in Hemidesmosome Assembly in Vitro", *Journal of Cell Science*, 105:753–764, 1993.

Langhofer, et al., "Matrix Signals Transduced by the $\alpha_6\beta_4$ Integrin Complex", *Mol. Biol. Cell*, 3(Suppl.):95a, 1992.

Riddelle, et al., "Hemidesmosomes in the Epithelial Cell Line 804G: Their Fate During Wound Closure, Mitosis and Drug Induced Reorganization of the Cytoskeleton", *Journal of Cell Science*, 103:475–490, 1992.

Riddelle, et al., "Substrate Attachment is Necessary for the Expression of Hemidesmosomal Proteins in Cultured Cells", *Mol. Biol. Cell*, 3:Suppl.:70a, 1992.

Riddelle, et al., "Dynamic Aspects of Hemidesmosomes in the Novel Epithelial Cell Line, 804G", *J. Cell Biol.*, 115:3:Pt.2:41a, 1991.

Riddelle, et al., "Formation of Hemidesmosomes in Vitro by a Transformed Rat Bladder Cell Line", *The Journal of Cell Biology*, 112:1:159–168, 1991.

(List continued on next page.)

*Primary Examiner*—Michael G. Wityshyn
*Assistant Examiner*—Kristin K. Larson
*Attorney, Agent, or Firm*—Knobbe, Martens, Olson & Bear

[57] ABSTRACT

A method for growing epithelial cells in vitro using soluble proteins secreted by 804G and NBT-II rat bladder carcinoma cells. These proteins stimulate cell attachment and hemidesmosome formation in cells grown in contact with the proteins. The protein is purified from conditioned medium by immunoaffinity chromatography using a monoclonal antibody generated against the protein. The purification of these proteins may be facilitated by culturing the cells under low serum or serum free conditions.

22 Claims, 1 Drawing Sheet

OTHER PUBLICATIONS

Riddelle, et al., "Hemidesmosomes in Cultured Cells", *J. Cell Biol.*, 111:5:Pt.2:2270, 1990.

Riddelle, et al., "Characterization of a Novel Cell–Substratum Attachment Device in Cultured Epithelial Cells", *J. Cell Biol.*, 109:4:Pt.2:201a, 1989.

Rousselle, et al., "Kalinin: An Epithelium–Specific Basement Membrane Adhesion Molecule That is a Component of Anchoring Filaments", *Journal of Cell Biology*, 114:3:567–576, 1991.

Schwarz, et al., "Desmosomes and Hemidesmosomes: Constitutive Molecular Components", *Annu. Rev. Cell Biol.*, 6:461–491, 1990.

Sonnenberg, et al., "Integrin $\alpha_6/\beta_4$ Complex is Located in Hemidesmosomes, Suggesting a Major Role in Epidermal Cell–Basement Membrane Adhesion", *The Journal of Cell Biology*, 113:(4):907–917, 1991.

Staehelin, "Structure and Function of Intercellular Junctions", *Dept. of Mol. Cellular and Developmental Biology, Univ. of Colorado*, Boulder, CO, 191–283.

Stepp, et al., "$\alpha_4\beta_4$ Integrin Heterodimer is a Component of Hemidesmosomes", *Proc. Natl. Acad. Sci. USA*, 87:8970–8974, 1990.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 1171 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

```
Thr Ser Arg Arg Glu Val Cys Asp Cys Asn Gly Lys Ser Arg Gln Cys
 1               5                  10                  15

Val Phe Asp Gln Glu His Leu Arg Gln Thr Gly Asn Gly Asn Arg Cys
                20                  25                  30

Leu Asn Cys Asn Asp Asn Thr Ala Gly Val His Cys Glu Arg Cys Arg
            35                  40                  45

Glu Gly Phe Tyr Arg Gln Arg Asp Arg Asp Arg Cys Leu Pro Cys Asn
        50                  55                  60

Cys His Ser Lys Gly Ser Leu Gly Ala Gly Cys Asp Asn Ser Gly Gln
65                  70                  75                  80

Cys Arg Cys Lys Pro Gly Val Val Gly Gln Arg Cys Asp Arg Cys Gln
                85                  90                  95

Pro Gly Phe His Met Leu Thr Asp Ala Gly Cys Thr Arg Asp Gln Arg
                100                 105                 110

Gln Leu Asp Ser Lys Cys Asp Cys Asp Pro Ala Gly Ile Ser Gly Pro
            115                 120                 125
```

| Cys | Asp | Ser | Arg | Arg | Cys | Val | Cys | Lys | Gly | Ala | Val | Thr | Gly | Glu | Arg |
|     |     | 130 |     |     |     | 135 |     |     |     | 140 |     |     |     |     |     |

| Cys | Asp | Arg | Cys | Arg | Ala | Gly | Tyr | Tyr | His | Leu | Asp | Arg | Ala | Asn | Pro |
| 145 |     |     |     |     | 150 |     |     |     | 155 |     |     |     |     |     | 160 |

| Glu | Gly | Cys | Thr | Gln | Cys | Phe | Cys | Tyr | Gly | Tyr | Ser | Asp | Ser | Cys | His |
|     |     |     |     | 165 |     |     |     |     | 170 |     |     |     |     | 175 |     |

| Thr | Ser | Ala | Asp | Phe | Ser | Val | His | Lys | Ile | Thr | Ser | Thr | Phe | Asn | Gln |
|     |     |     | 180 |     |     |     |     | 185 |     |     |     |     | 190 |     |     |

| Asp | Glu | Glu | Val | Gly | Lys | Gln | Phe | Arg | Glu | Asn | Trp | Ala | Pro | Ala | Lys |
|     |     | 195 |     |     |     |     | 200 |     |     |     |     | 205 |     |     |     |

| Leu | His | Trp | Ser | Pro | Arg | His | Gln | Asp | Ile | Phe | Ser | Ser | Cys | Pro | Lys |
|     |     | 210 |     |     |     |     | 215 |     |     |     | 220 |     |     |     |     |

| Ile | Arg | Pro | Ser | Leu | Phe | Arg | Ala | Pro | Ala | Lys | Phe | Leu | Gly | Asn | Gln |
| 225 |     |     |     |     | 230 |     |     |     |     | 235 |     |     |     |     | 240 |

| Gln | Val | Ser | Tyr | Gly | Gln | Ser | Leu | Ser | Phe | Asp | Tyr | Arg | Val | Asp | Arg |
|     |     |     |     | 245 |     |     |     |     | 250 |     |     |     |     | 255 |     |

| Gly | Gly | Arg | His | Pro | Ser | Ala | Tyr | Asp | Val | Ile | Leu | Glu | Gly | Ala | Gly |
|     |     |     |     | 260 |     |     |     |     | 265 |     |     |     |     | 270 |     |

| Leu | Gln | Ile | Arg | Ala | Pro | Val | Met | Pro | Pro | Arg | Lys | Thr | Leu | Pro | Cys |
|     |     |     |     | 275 |     |     |     | 280 |     |     |     |     | 285 |     |     |

| Gly | Ile | Thr | Lys | Thr | Tyr | Thr | Phe | Arg | Leu | Asn | Glu | His | Pro | Ser | Ser |
|     |     |     | 290 |     |     |     |     | 295 |     |     |     |     | 300 |     |     |

| His | Trp | Ser | Pro | Gln | Leu | Ser | Tyr | Phe | Glu | Tyr | Arg | Arg | Leu | Leu | Arg |
| 305 |     |     |     |     |     | 310 |     |     |     |     | 315 |     |     |     | 320 |

| Asn | Leu | Thr | Ala | Leu | Leu | Ile | Arg | Ala | Thr | Tyr | Gly | Glu | Tyr | Ser | Thr |
|     |     |     |     |     | 325 |     |     |     |     | 330 |     |     |     |     | 335 |

| Gly | Tyr | Ile | Asp | Asn | Val | Thr | Leu | Ile | Ser | Ala | Arg | Pro | Val | Ser | Gly |
|     |     |     |     | 340 |     |     |     |     | 345 |     |     |     |     | 350 |     |

| Ala | Gln | Ser | Pro | Trp | Val | Glu | Arg | Cys | Val | Cys | Pro | Ala | Gly | Tyr | Lys |
|     |     |     | 355 |     |     |     |     | 360 |     |     |     |     | 365 |     |     |

| Gly | Gln | Phe | Cys | Gln | Glu | Cys | Ala | Ser | Gly | Tyr | Lys | Arg | Asp | Ser | Val |
|     |     | 370 |     |     |     |     | 375 |     |     |     |     | 380 |     |     |     |

| Lys | Thr | Cys | Pro | Phe | Gly | Thr | Cys | Val | Pro | Cys | Asn | Cys | Gln | Gly | Gly |
| 385 |     |     |     |     | 390 |     |     |     |     | 395 |     |     |     |     | 400 |

| Gly | Ala | Cys | Asp | Pro | Asp | Thr | Gly | Asp | Cys | Tyr | Ser | Gly | Asp | Glu | Asn |
|     |     |     |     | 405 |     |     |     |     | 410 |     |     |     |     | 415 |     |

| Pro | Asp | Ile | Glu | Cys | Ala | Asp | Cys | Pro | Leu | Val | Ser | Ile | Asn | Asp | Pro |
|     |     |     |     | 420 |     |     |     |     | 425 |     |     |     |     | 430 |     |

| His | Asp | Pro | Arg | Ser | Cys | Lys | Pro | Cys | Pro | Cys | His | Asn | Gly | Phe | Ser |
|     |     |     | 435 |     |     |     |     | 440 |     |     |     |     | 445 |     |     |

| Cys | Ser | Val | Met | Pro | Glu | Thr | Glu | Glu | Val | Val | Cys | Asn | Asn | Cys | Pro |
|     | 450 |     |     |     |     | 455 |     |     |     |     | 460 |     |     |     |     |

| Pro | Gly | Val | Thr | Gly | Ala | Arg | Cys | Glu | Leu | Cys | Ala | Asp | Gly | Phe | Phe |
| 465 |     |     |     |     | 470 |     |     |     |     | 475 |     |     |     |     | 480 |

| Gly | Asp | Pro | Phe | Gly | Glu | Arg | Gly | Pro | Val | Thr | Gly | Cys | Gln | Arg | Cys |
|     |     |     |     | 485 |     |     |     |     | 490 |     |     |     |     | 495 |     |

| Gln | Cys | Asn | Asn | Asn | Val | Asp | Pro | Ser | Ala | Ser | Gly | Asn | Cys | Asp | Gln |
|     |     |     |     | 500 |     |     |     |     | 505 |     |     |     |     | 510 |     |

| Leu | Thr | Gly | Arg | Cys | Leu | Lys | Cys | Ile | Tyr | Asn | Thr | Pro | Gly | Ile | Tyr |
|     |     |     | 515 |     |     |     |     | 520 |     |     |     |     | 525 |     |     |

| Cys | Asp | Gln | Cys | Lys | Ala | Gly | Gln | Phe | Glu | Thr | Pro | Leu | Ala | Pro | Asn |
|     |     | 530 |     |     |     |     | 535 |     |     |     |     | 540 |     |     |     |

| Pro | Ala | Asp | Lys | Cys | Arg | Ala | Cys | Asn | Cys | Asn | Pro | Val | Gly | Ser | Glu |

```
545                     550                      555                      560
Pro  Gly  Glu  Cys  Arg  Ser  Asp  Gly  Ser  Cys  Val  Cys  Lys  Pro  Gly  Phe
               565                      570                      575
Gly  Gly  Leu  Asn  Cys  Arg  Thr  Ala  Ala  Ala  Leu  Thr  Ser  Cys  Pro  Ala
               580                      585                      590
Cys  Tyr  Asn  Gln  Val  Lys  Thr  Gln  Met  Asp  Gln  Phe  Ala  Gln  Gln  Leu
               595                      600                      605
Gln  Asn  Leu  Glu  Ala  Leu  Val  Ser  Lys  Ala  Gln  Gly  Gly  Asn  Gly  Ala
          610                      615                      620
Val  Pro  Gln  Arg  Gly  Arg  Glu  Gly  Arg  Ile  Glu  Gln  Ala  Glu  Gln  Ala
625                      630                      635                      640
Leu  Asp  Arg  Ile  Leu  Arg  Glu  Ala  Gln  Ile  Ser  Glu  Gly  Ala  Met  Arg
               645                      650                      655
Ala  Leu  Ser  Leu  Gln  Leu  Ala  Lys  Ala  Arg  Ser  Gln  Glu  Asn  Asn  Tyr
               660                      665                      670
Gln  Asn  Arg  Leu  Asp  Asp  Leu  Lys  Met  Thr  Val  Glu  Arg  Ile  Arg  Ala
               675                      680                      685
Leu  Gly  Arg  Gln  Tyr  Gln  Asn  Arg  Val  Gln  Asp  Thr  Ser  Arg  Leu  Ile
          690                      695                      700
Ser  Gln  Met  Leu  Leu  Ser  Leu  Ala  Glu  Ser  Glu  Ala  Ser  Leu  Gln  Asn
705                      710                      715                      720
Thr  Asn  Ile  His  Ser  Ser  Glu  His  Tyr  Val  Gly  Pro  Asn  Gly  Phe  Lys
               725                      730                      735
Ser  Leu  Ala  Gln  Glu  Ala  Ala  Arg  Leu  Ala  Asp  Ser  His  Val  Glu  Ser
               740                      745                      750
Ala  Asn  Ser  Met  Lys  Gln  Leu  Thr  Arg  Glu  Thr  Glu  Asp  Tyr  Ser  Lys
               755                      760                      765
Gln  Ala  Leu  Ser  Leu  Ala  Arg  Lys  Pro  Leu  Ser  Gly  Gly  Gly  Gly  Ser
          770                      775                      780
Gly  Val  Leu  Asp  Ser  Ser  Val  Val  Gln  Gly  Leu  Tyr  Gly  Lys  Ile  Arg
785                      790                      795                      800
Glu  Asn  Gln  Val  Pro  Ala  Gln  Gln  Leu  Ser  Arg  Glu  Gly  Thr  Gln  Ala
                    805                      810                      815
Asp  Ile  Glu  Ala  Asp  Arg  Ser  Tyr  Gln  His  Ser  Leu  Arg  Leu  Leu  Asp
               820                      825                      830
Ser  Ala  Ser  Arg  Leu  Gln  Gly  Ile  Arg  Asp  Ser  Ser  Phe  Gln  Ala  Glu
          835                      840                      845
Ala  Lys  Arg  Ile  Arg  Gln  Lys  Ala  Asp  Ser  Leu  Ser  Asn  Leu  Val  Thr
     850                      855                      860
Lys  Gln  Met  Asp  Ala  Phe  Thr  Ser  Val  Arg  Asn  Asn  Leu  Gly  Asn  Trp
865                      870                      875                      880
Glu  Lys  Gln  Thr  Arg  Gln  Leu  Leu  Gln  Thr  Gly  Lys  Asp  Arg  Arg  Gln
                    885                      890                      895
Thr  Ser  Asp  Gln  Leu  Leu  Ser  Arg  Ala  Ser  Leu  Leu  Lys  Met  Arg  Ala
               900                      905                      910
Gln  Glu  Ala  Leu  Ser  Met  Gly  Asn  Ala  Thr  Phe  Tyr  Glu  Val  Glu  Asn
          915                      920                      925
Ile  Leu  Lys  Asp  Leu  Arg  Glu  Phe  Asp  Leu  Gln  Val  Glu  Asp  Arg  Lys
     930                      935                      940
Ala  Glu  Ala  Glu  Glu  Ala  Met  Lys  Arg  Leu  Ser  Tyr  Ile  Ser  Gln  Lys
945                      950                      955                      960
Val  Ala  Val  Ala  Ser  Asp  Lys  Thr  Gln  Gln  Ala  Glu  Thr  Ala  Leu  Gly
               965                      970                      975
```

```
Ser  Ala  Ala  Ala  Asp  Thr  Gln  Arg  Ala  Lys  Asn  Ala  Ala  Thr  Glu  Ala
               980                      985                      990

Leu  Glu  Ile  Thr  Ser  Glu  Ile  Glu  Gln  Glu  Ile  Gly  Ser  Leu  Asn  Leu
          995                     1000                    1005

Glu  Ala  Asn  Val  Thr  Ala  Asp  Gly  Ala  Leu  Ala  Met  Glu  Lys  Gly  Leu
          1010                    1015                    1020

Ala  Thr  Leu  Lys  Ser  Glu  Met  Arg  Glu  Val  Glu  Gly  Glu  Leu  Ala  Arg
1025                     1030                    1035                     1040

Lys  Glu  Leu  Glu  Phe  His  Thr  Val  Lys  Asp  Ser  Leu  Gln  Leu  Val  Ile
               1045                     1050                    1055

Thr  Glu  Ala  Gln  Gln  Ala  Asp  Ala  Arg  Ala  Lys  Ser  Thr  Gly  Val  Thr
               1060                     1065                    1070

Ile  Gln  Asp  Thr  Leu  Asn  Thr  Leu  Glu  Gly  Ile  Leu  Arg  Leu  Ile  Asp
          1075                    1080                    1085

Gln  Pro  Asp  Ala  Val  Asp  Glu  Glu  Gly  Leu  Met  Leu  Leu  Glu  Gln  Glu
          1090                    1095                    1100

Gln  Asn  Gln  Ala  Lys  Thr  Gln  Ile  Asn  Ser  Arg  Leu  Arg  Pro  Leu  Met
1105                     1110                    1115                     1120

Ser  Glu  Leu  Glu  Asp  Arg  Ala  Arg  Arg  Gln  Ser  Asn  His  Leu  His  Leu
               1125                     1130                    1135

Leu  Glu  Thr  Ser  Ile  Asp  Gly  Ile  Leu  Ala  Asp  Val  Lys  Asn  Leu  Glu
               1140                     1145                    1150

Asn  Ile  Arg  Asp  Asn  Leu  Pro  Pro  Gly  Cys  Tyr  Asn  Thr  Gln  Ala  Leu
          1155                    1160                    1165

Glu  Gln  Gln
     1170
```

( 2 ) INFORMATION FOR SEQ ID NO:2:

( i ) SEQUENCE CHARACTERISTICS:
       ( A ) LENGTH: 770 amino acids
       ( B ) TYPE: amino acid
       ( C ) STRANDEDNESS: single
       ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i i ) IMMEDIATE SOURCE:
       ( B ) CLONE: 150 kD ( x i ) SEQUENCE DESCRIPTION: SEQ ID NO:2:

```
Glu  Phe  Glu  Thr  Leu  Gln  Glu  Lys  Ala  Gln  Val  Asn  Ser  Arg  Lys  Ala
1                   5                    10                       15

Gln  Thr  Leu  Tyr  Asn  Asn  Ile  Asp  Thr  Thr  Ile  Gln  Asn  Ala  Lys  Glu
               20                    25                       30

Leu  Asp  Met  Lys  Ile  Lys  Asn  Ile  Leu  Thr  Asn  Val  His  Ile  Leu  Leu
          35                    40                       45

Lys  Gln  Ile  Ala  Arg  Pro  Gly  Gly  Glu  Gly  Met  Asp  Leu  Pro  Val  Gly
     50                    55                       60

Asp  Trp  Ser  Arg  Glu  Ser  Ala  Glu  Arg  His  Gly  His  Val  Ala  Glu  Ser
65                       70                       75                       80

Arg  Gly  Arg  Asp  Phe  Lys  Lys  His  Leu  Gln  Glu  Ala  Glu  Ala  Gln  Lys
               85                    90                       95

Met  Glu  Ala  Gln  Leu  Leu  Leu  Asn  Arg  Ile  Arg  Thr  Trp  Leu  Glu  Ser
```

-continued

```
                    100                         105                         110
His  Gln  Val  Glu  Asn  Asn  Gly  Leu  Leu  Lys  Asn  Ile  Arg  Asp  Ser  Leu
          115                         120                        125
Asn  Asp  Tyr  Glu  Ala  Lys  Leu  Gln  Asp  Leu  Arg  Ser  Val  Leu  Gln  Glu
     130                         135                        140
Ala  Ala  Ala  Gln  Gly  Lys  Gln  Ala  Thr  Gly  Leu  Asn  His  Glu  Asn  Glu
145                              150                        155                           160
Gly  Val  Leu  Gly  Ala  Ile  Gln  Arg  Gln  Met  Lys  Glu  Met  Asp  Ser  Leu
               165                        170                        175
Lys  Lys  Tyr  Leu  Thr  Glu  His  Leu  Ala  Thr  Ala  Asp  Ala  Ser  Leu  Leu
               180                        185                        190
Gln  Thr  Asn  Ser  Leu  Leu  Gln  Arg  Met  Asp  Thr  Ser  Gln  Lys  Glu  Tyr
          195                         200                        205
Glu  Ser  Leu  Ala  Ala  Ala  Leu  Asn  Gly  Ala  Arg  Gln  Glu  Leu  Asn  Asp
     210                         215                        220
Gln  Val  Arg  Glu  Leu  Ser  Arg  Ser  Gly  Gly  Lys  Ala  Pro  Leu  Val  Ala
225                              230                        235                           240
Glu  Ala  Glu  Lys  His  Ala  Gln  Ser  Leu  Gln  Glu  Leu  Ala  Lys  Gln  Leu
                    245                        250                        255
Glu  Glu  Ile  Lys  Arg  Asn  Thr  Ser  Gly  Asp  Glu  Ser  Val  Arg  Cys  Val
               260                        265                        270
Val  Asp  Ala  Ala  Thr  Ala  Tyr  Glu  Ser  Ile  Leu  Asn  Ala  Ile  Arg  Ala
          275                         280                        285
Ala  Glu  Asp  Ala  Ala  Gly  Lys  Ala  Asp  Ser  Ala  Ser  Glu  Ser  Ala  Phe
     290                         295                        300
Gln  Thr  Val  Ile  Lys  Glu  Asp  Leu  Pro  Arg  Arg  Ala  Lys  Thr  Leu  Ser
305                              310                        315                           320
Ser  Asp  Ser  Glu  Glu  Leu  Leu  Asn  Glu  Ala  Lys  Met  Thr  Arg  Lys  Arg
                    325                        330                        335
Leu  Gln  Gln  Glu  Ile  Asn  Pro  Ala  Leu  Asn  Ser  Leu  Gln  Gln  Thr  Leu
               340                        345                        350
Lys  Thr  Val  Ser  Val  Gln  Lys  Asp  Leu  Leu  Asp  Ala  Asn  Val  Thr  Ala
          355                         360                        365
Val  Arg  Asn  Asp  Leu  Arg  Gly  Ile  Gln  Arg  Gly  Asp  Ile  Asp  Ser  Val
     370                         375                        380
Val  Ser  Gly  Ala  Lys  Ser  Met  Val  Arg  Lys  Ala  Asn  Gly  Ile  Thr  Ser
385                              390                        395                           400
Glu  Val  Leu  Asp  Gly  Ser  Ala  Pro  Ser  Arg  Arg  Ile  Trp  Glu  Gly  Leu
                    405                        410                        415
Arg  Thr  Ala  Thr  Gly  Cys  Thr  Arg  His  Glu  Asp  Phe  Asn  Lys  Ala  Leu
               420                        425                        430
Ile  Asp  Ala  Asn  Asn  Ser  Val  Lys  Lys  Leu  Thr  Lys  Lys  Leu  Pro  Asp
          435                         440                        445
Leu  Phe  Val  Lys  Ile  Glu  Ser  Ile  Asn  Gln  Gln  Leu  Leu  Pro  Leu  Gly
     450                         455                        460
Asn  Ile  Ser  Asp  Asn  Val  Asp  Arg  Ile  Arg  Glu  Leu  Ile  Thr  Gln  Ala
465                              470                        475                           480
Arg  Asp  Ala  Ala  Asn  Lys  Val  Ala  Ile  Pro  Met  Arg  Phe  Asn  Gly  Lys
                    485                        490                        495
Ser  Gly  Val  Glu  Val  Arg  Leu  Pro  Asn  Asp  Leu  Glu  Asp  Leu  Lys  Gly
               500                        505                        510
Tyr  Thr  Ser  Leu  Ser  Leu  Phe  Leu  Gln  Arg  Pro  Asp  Leu  Arg  Glu  Asn
          515                         520                        525
```

-continued

```
Gly  Gly  Thr  Glu  Asp  Met  Phe  Val  Met  Tyr  Leu  Gly  Asn  Lys  Asp  Ala
     530                 535                      540

Ser  Lys  Asp  Tyr  Ile  Gly  Ile  Gly  Gly  Cys  Arg  Trp  Pro  Ala  Asp  Val
545                      550                 555                           560

Cys  Leu  Gln  Pro  Gly  Gly  Pro  Arg  Ser  Val  Ser  Ser  Asp  Arg  Ser  Gly
                    565                      570                      575

Leu  Thr  Glu  Ser  Glu  Ser  Gln  Glu  Ala  Val  Met  Asp  Arg  Val  Lys  Phe
               580                 585                           590

Gln  Arg  Ile  Tyr  Gln  Phe  Ala  Lys  Leu  Asn  Tyr  Thr  Lys  Glu  Ala  Thr
          595                 600                      605

Ser  Asn  Lys  Pro  Lys  Ala  Pro  Ala  Val  Tyr  Asp  Leu  Glu  Gly  Gly  Ser
     610                 615                      620

Ser  Asn  Thr  Leu  Leu  Asn  Leu  Asp  Pro  Glu  Asp  Ala  Val  Phe  Tyr  Val
625                      630                 635                          640

Gly  Gly  Tyr  Pro  Pro  Asp  Phe  Glu  Leu  Pro  Ser  Arg  Leu  Arg  Phe  Pro
                    645                 650                      655

Pro  Tyr  Lys  Gly  Cys  Ile  Glu  Leu  Asp  Asp  Leu  Asn  Glu  Asn  Val  Leu
               660                 665                      670

Ser  Leu  Tyr  Asn  Phe  Lys  Thr  Thr  Phe  Asn  Leu  Asn  Thr  Thr  Glu  Val
          675                 680                      685

Glu  Pro  Cys  Arg  Arg  Arg  Lys  Glu  Glu  Ser  Asp  Lys  Asn  Tyr  Phe  Glu
     690                 695                      700

Gly  Thr  Gly  Tyr  Ala  Arg  Ile  Pro  Thr  Gln  Pro  Asn  Ala  Pro  Phe  Pro
705                      710                 715                          720

Asn  Phe  Ile  Gln  Thr  Ile  Gln  Thr  Thr  Val  Ala  Arg  Gly  Leu  Leu  Phe
                    725                 730                      735

Phe  Ala  Glu  Asn  Gln  Asp  Asn  Phe  Ile  Ser  Leu  Asn  Ile  Glu  Asp  Gly
               740                 745                      750

Asn  Leu  Met  Val  Arg  Tyr  Lys  Leu  Asn  Ser  Glu  Pro  Pro  Lys  Glu  Lys
          755                 760                      765

Gly  Ile
770
```

( 2 ) INFORMATION FOR SEQ ID NO:3:

( i ) SEQUENCE CHARACTERISTICS:
        ( A ) LENGTH: 360 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i i ) IMMEDIATE SOURCE:
        ( B ) CLONE: laminin A ( x i ) SEQUENCE DESCRIPTION: SEQ ID NO:3:

```
Lys  Phe  Asp  Thr  Val  Ser  Glu  Gln  Lys  Leu  Gln  Ala  Glu  Lys  Asn  Ile
1                   5                    10                           15

Lys  Asp  Ala  Gly  Asn  Phe  Leu  Ile  Asn  Gly  Asp  Leu  Thr  Leu  Asn  Gln
               20                  25                       30

Ile  Asn  Gln  Lys  Leu  Asp  Asn  Leu  Arg  Asp  Ala  Leu  Asn  Glu  Leu  Asn
          35                  40                       45

Ser  Phe  Asn  Lys  Asn  Val  Asp  Glu  Glu  Leu  Pro  Val  Arg  Glu  Asp  Gln
```

|     |     |     | 50  |     |     | 55  |     |     |     |     | 60  |     |     |     |
| --- | --- | --- | --- | --- | --- | --- | --- | --- | --- | --- | --- | --- | --- | --- |
| His | Lys | Glu | Ala | Asp | Ala | Leu | Thr | Asp | Gln | Ala | Glu | Gln | Lys | Ala | Ala |
| 65  |     |     |     |     | 70  |     |     |     | 75  |     |     |     |     | 80  |
| Glu | Leu | Ala | Ile | Lys | Ala | Gln | Asp | Leu | Ala | Ala | Gln | Tyr | Thr | Asp | Met |
|     |     |     |     | 85  |     |     |     | 90  |     |     |     |     | 95  |     |
| Thr | Ala | Ser | Ala | Glu | Pro | Ala | Ile | Lys | Ala | Ala | Thr | Ala | Tyr | Ser | Gly |
|     |     |     | 100 |     |     |     | 105 |     |     |     |     | 110 |     |     |
| Ile | Val | Glu | Ala | Val | Glu | Ala | Ala | Gln | Lys | Leu | Ser | Gln | Asp | Ala | Ile |
|     |     | 115 |     |     |     |     | 120 |     |     |     |     | 125 |     |     |
| Ser | Ala | Ala | Gly | Asn | Ala | Thr | Asp | Lys | Thr | Asp | Gly | Ile | Glu | Glu | Arg |
|     | 130 |     |     |     |     | 135 |     |     |     |     | 140 |     |     |     |
| Ala | His | Leu | Ala | Asp | Thr | Gly | Ser | Thr | Asp | Leu | Leu | Gln | Arg | Ala | Arg |
| 145 |     |     |     |     | 150 |     |     |     |     | 155 |     |     |     |     | 160 |
| Gln | Ser | Leu | Gln | Lys | Val | Gln | Asp | Asp | Leu | Glu | Pro | Arg | Leu | Asn | Ala |
|     |     |     |     | 165 |     |     |     |     | 170 |     |     |     |     | 175 |     |
| Ser | Ala | Gly | Lys | Val | Gln | Lys | Ile | Ser | Ala | Val | Asn | Asn | Ala | Thr | Glu |
|     |     |     | 180 |     |     |     |     | 185 |     |     |     | 190 |     |     |     |
| His | Gln | Leu | Lys | Asp | Ile | Asn | Lys | Leu | Ile | Asp | Gln | Leu | Pro | Ala | Glu |
|     |     | 195 |     |     |     |     | 200 |     |     |     |     | 205 |     |     |     |
| Ser | Gln | Arg | Asp | Met | Trp | Lys | Asn | Ser | Asn | Ala | Asn | Ala | Ser | Asp | Glu |
|     | 210 |     |     |     |     | 215 |     |     |     |     | 220 |     |     |     |
| Ala | Glu | Ile | Leu | Lys | Asn | Val | Leu | Glu | Ile | Leu | Glu | Pro | Val | Ser | Val |
| 225 |     |     |     |     | 230 |     |     |     |     | 235 |     |     |     |     | 240 |
| Gln | Thr | Pro | Lys | Glu | Leu | Glu | Lys | Ala | His | Gly | Ile | Asn | Arg | Asp | Leu |
|     |     |     |     | 245 |     |     |     |     | 250 |     |     |     |     | 255 |     |
| Asp | Leu | Thr | Asn | Lys | Asp | Val | Ser | Gln | Ala | Asn | Lys | Gln | Leu | Asp | Asp |
|     |     |     | 260 |     |     |     |     | 265 |     |     |     | 270 |     |     |     |
| Val | Glu | Gly | Ser | Val | Ser | Lys | Leu | Asn | Glu | Leu | Ala | Glu | Asp | Ile | Glu |
|     |     | 275 |     |     |     |     | 280 |     |     |     |     | 285 |     |     |     |
| Glu | Gln | Gln | His | Arg | Val | Gly | Ser | Gln | Ser | Arg | Gln | Leu | Gly | Gln | Glu |
|     | 290 |     |     |     |     | 295 |     |     |     |     | 300 |     |     |     |
| Ile | Glu | Asn | Leu | Lys | Ala | Gln | Val | Glu | Ala | Ala | Arg | Gln | Leu | Ala | Asn |
| 305 |     |     |     |     | 310 |     |     |     |     | 315 |     |     |     |     | 320 |
| Ser | Ile | Lys | Val | Gly | Val | Asn | Phe | Lys | Pro | Ser | Thr | Ile | Leu | Glu | Leu |
|     |     |     |     | 325 |     |     |     |     | 330 |     |     |     |     | 335 |     |
| Lys | Thr | Pro | Glu | Lys | Thr | Lys | Leu | Leu | Ala | Thr | Arg | Thr | Asn | Leu | Ser |
|     |     |     | 340 |     |     |     |     | 345 |     |     |     | 350 |     |     |     |
| Thr | Tyr | Phe | Arg | Thr | Thr | Glu | Pro |     |     |     |     |     |     |     |     |
|     |     | 355 |     |     |     |     | 360 |     |     |     |     |     |     |     |     |

( 2 ) INFORMATION FOR SEQ ID NO:4:

( i ) SEQUENCE CHARACTERISTICS:
    ( A ) LENGTH: 337 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i i ) IMMEDIATE SOURCE:
    ( B ) CLONE: merosin ( x i ) SEQUENCE DESCRIPTION: SEQ ID NO:4:

| | | | | | | | | | | | | | | |
|---|---|---|---|---|---|---|---|---|---|---|---|---|---|---|
| Glu<br>1 | Leu | Lys | His | Leu<br>5 | Leu | Ser | Pro | Gln | Arg<br>10 | Ala | Pro | Glu | Arg | Leu<br>15 | Ile |
| Gln | Leu | Ala | Glu<br>20 | Gly | Asn | Leu | Asn | Thr<br>25 | Leu | Val | Thr | Glu | Met<br>30 | Asn | Glu |
| Leu | Leu | Thr<br>35 | Arg | Ala | Thr | Lys | Val<br>40 | Thr | Ala | Asp | Gly | Glu<br>45 | Gln | Thr | Gly |
| Gln | Asp<br>50 | Ala | Glu | Arg | Thr | Asn<br>55 | Thr | Arg | Ala | Lys | Ser<br>60 | Leu | Gly | Glu | Phe |
| Ile<br>65 | Lys | Glu | Leu | Ala | Arg<br>70 | Asp | Ala | Glu | Ala | Val<br>75 | Asn | Glu | Lys | Ala | Ile<br>80 |
| Lys | Leu | Asn | Glu | Thr<br>85 | Leu | Gly | Thr | Arg | Asp<br>90 | Glu | Ala | Phe | Glu | Arg<br>95 | Asn |
| Leu | Glu | Gly | Leu<br>100 | Gln | Lys | Glu | Ile | Asp<br>105 | Gln | Met | Ile | Lys | Glu<br>110 | Leu | Arg |
| Arg | Lys | Asn<br>115 | Leu | Glu | Thr | Gln | Lys<br>120 | Glu | Ile | Ala | Glu | Asp<br>125 | Glu | Leu | Val |
| Ala | Ala<br>130 | Glu | Ala | Leu | Leu | Lys<br>135 | Lys | Val | Lys | Lys | Leu<br>140 | Phe | Gly | Glu | Ser |
| Arg<br>145 | Gly | Glu | Asn | Glu | Glu<br>150 | Met | Glu | Lys | Asp | Leu<br>155 | Arg | Glu | Lys | Leu | Ala<br>160 |
| Asp | Tyr | Lys | Asn | Lys<br>165 | Val | Asp | Asp | Ala | Trp<br>170 | Asp | Leu | Leu | Arg | Glu<br>175 | Ala |
| Thr | Asp | Lys | Ile<br>180 | Arg | Glu | Ala | Asn | Arg<br>185 | Leu | Phe | Ala | Val | Asn<br>190 | Gln | Lys |
| Asn | Met | Thr<br>195 | Ala | Leu | Glu | Lys | Lys<br>200 | Lys | Glu | Ala | Val | Glu<br>205 | Ser | Gly | Lys |
| Arg | Gln<br>210 | Ile | Gln | Asn | Thr | Leu<br>215 | Lys | Glu | Gly | Asn | Asp<br>220 | Ile | Leu | Asp | Glu |
| Ala<br>225 | Asn | Arg | Leu | Ala | Asp<br>230 | Glu | Ile | Asn | Ser | Ile<br>235 | Ile | Asp | Tyr | Val | Glu<br>240 |
| Asp | Ile | Gln | Thr | Lys<br>245 | Leu | Pro | Pro | Met | Ser<br>250 | Glu | Glu | Leu | Asn | Asp<br>255 | Lys |
| Ile | Asp | Asp | Leu<br>260 | Ser | Gln | Glu | Ile | Lys<br>265 | Asp | Arg | Lys | Leu | Ala<br>270 | Glu | Lys |
| Val | Ser | Gln<br>275 | Ala | Glu | Ser | His | Ala<br>280 | Ala | Gln | Leu | Asn | Asp<br>285 | Ser | Ser | Ala |
| Val | Leu | Asp<br>290 | Gly | Ile | Leu | Asp<br>295 | Glu | Ala | Lys | Asn | Ile<br>300 | Ser | Phe | Asn | Ala |
| Thr<br>305 | Ala | Ala | Phe | Lys | Ala<br>310 | Tyr | Ser | Asn | Ile | Lys<br>315 | Asp | Tyr | Ile | Asp | Glu<br>320 |
| Ala | Glu | Lys | Val | Ala<br>325 | Lys | Glu | Ala | Lys | Asp<br>330 | Leu | Ala | His | Glu | Ala<br>335 | Thr |
| Lys | | | | | | | | | | | | | | | |

(2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:5:

```
Ala Gln Gln Pro Ala Ser Arg Gly Ala Asp Tyr Pro Pro Val Gly Asp
 1               5                  10                  15
```

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:6:

```
Ile Glu Gly Glu Ile Phe Asp Phe Ser Thr Tyr Tyr Leu Gly Gly Ile
 1               5                  10                  15
Pro Ile
```

(2) INFORMATION FOR SEQ ID NO:7:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:7:

```
Ser Pro Gly Thr Tyr Met Gly Leu Leu His His Val Ser Val Ile Ser
 1               5                  10                  15
Asp Thr Ser Gly Leu
              20
```

PROMOTION OF EPITHELIAL CELL ADHESION AND HEMIDESMOSOME ASSEMBLY BY A LAMININ-LIKE MOLECULE

CROSS-REFERENCE TO RELATED APPLICATIONS

This application is a continuation-in-part of U.S. application Ser. No. 08/151,134, filed Nov. 12, 1993, now U.S. Pat. No. 5,422,264.

STATEMENT OF GOVERNMENT SUPPORT

This research was supported by National Institutes of Health Grants GM 46902 and DE 10063. The government may have certain rights in the invention.

BACKGROUND

When organs of the body are formed, they develop in neatly organized arrays. Often, cell groups of one kind are separated from cells of another kind by strips of connective tissue called basement membranes. In skin, for instance, the superficial layer of epidermal cells adheres to the underlying basement membrane. This skin basement membrane acts as a barrier between the epidermal cells on the outside, and the dermal cells underneath. A similar arrangement of cells occurs in the lining of the gut.

Basement membranes have been implicated in the growth, attachment, migration, repair, and differentiation of their overlying cell populations. Three layers have been defined in basement membranes: a) the lamina lucida, an electron microscope-clear region that resides in close approximation to the overlying cells; b) the lamina densa, an electron dense region of 20–300 nm in width; and c) the sublamina densa that contains anchoring fibrils, microfibrillar bundles and collagen fibers.

Many different types of compounds have now been localized to the basement membrane. Some of these compounds are laminin, collagen IV and heparin sulfate proteoglycans (Verrando et al. *Exp. Cell Res.*, 170:116–128, 1987). In addition, specific basement membranes have been found to possess other compounds, such as nidogen and entactin.

The principal cell adhesion receptor that epidermal cells use to attach to the basement membrane is called $\alpha_6\beta_4$. This transmembrane receptor is formed by a combination of two protein moieties $\alpha_6$ and $\beta_4$. The $\alpha_6$ and $\beta_4$ proteins are derived from different genes that have been found to be part of the integrin family.

Integrins are a versatile family of cell adhesion receptors. So far, approximately twenty members of this family have been discovered. These molecules are involved in many types of cell adhesion phenomena in the body. Integrins are signalling molecules that can translate environmental cues into intracellular instructions. Further, integrins can also transmit signals in the reverse direction, from the cell interior to the exterior. This has been illustrated in non-adherent cells, such as lymphocytes.

Stimulation of the T-cell antigen receptor, or of the CD3 complex, augments the affinity of certain integrins for the components to which they bind. Unfortunately, in adherent cells, changes in the affinities of integrins have been more difficult to demonstrate. However, affinity modulation of one integrin in differentiating epidermal keratinocytes has been described by Adams et al. (*Cell,* 63:425–435, 1990). For this reason, modifications of cell status initiated by activation or differentiation of other receptors may influence integrin affinity, and, ultimately, the adhesive behavior of cells. Further, as a consequence of adhering to a surface, an integrin may actively contribute to modifying cell shape or migration.

Many epithelial cells interact with the underlying extracellular matrix via a junction called the hemidesmosome (Staehelin, *Structure and Function of Intercellular Junctions*, Department of Molecular, Cellular and Developmental Biology, University of Colorado, Boulder, Colo., 191–283, 1974). Over the last few years there has been considerable progress in the biochemical characterization of this junction (Schwarz, et al., *Annu. Rev. Cell Biol.,* 6:461–491, 1990). The hemidesmosome, with its associated structures such as intermediate filaments and anchoring fibrils, forms an adhesion complex. Disruptions of the epithelial-connective tissue interaction is often accompanied by a disruption of the hemidesmosome complex. For example, in certain blistering skin diseases such as junctional epidermolysis bullosa where epithelial cell-connective tissue interactions are abnormal, it has been proposed that there is a biochemical modification in or loss of a basement membrane zone-associated component of the hemidesmosome.

Two high molecular weight intracellular components of the hemidesmosome have been identified and characterized with the aid of antisera from patients suffering from bullous pemphigoid. This autoimmune disease results in the simultaneous disruption of epithelial cell-connective tissue interactions and the loss of hemidesmosome integrity (Chapman et al. *Br. J. Dermatol,* 123:137–144, 1990). Accordingly, it was discovered that bullous pemphigoid patients were producing antibodies against hemidesmosome components. Two hemidesmosome related bullous pemphigoid (BP) antigens have been previously described (Klatte, et al., *J. Cell Biol.,* 109:3377–3390, 1989).

One BP antigen is a 230 kD polypeptide that may act as an anchor for cytoskeletal elements in the hemidesmosomal plaque (Jones and Green, *Curr. Opin. Cell Biol.,* 3:127–132, 1991). A second BP antigen is a type II membrane protein that possesses a collagen-like extracellular domain (Giudice, et al., *J. Clin. Invest.,* 87:734–738, 1991; Hopkinson, et al., *J. Invest. Dermatol.,* 3:264–270, 1992). In addition, it has been demonstrated that the interaction of the hemidesmosome with the underlying connective tissue involves the $\alpha_6\beta_4$ integrin heterodimer (Stepp, et al., *Proc. Natl. Acad. Sci. USA,* 87:8970–8974, 1990; Jones, et al., *Cell Regulation,* 2:427–438, 1991; Sonnenberg, et al., *J. Cell Biol.,* 113:907–917, 1991; Kurpakus, et al., *J. Cell Biol.,* 115:1737–1750, 1991). The $\alpha_6\beta_4$ heterodimer has been localized to hemidesmosomes along the basal surfaces of the rat bladder carcinoma cell line 804G (Jones et al. *Cell Regulation,* 2:27–438, 1991). These results suggested that integrins (e.g. $\alpha_6\beta_4$) may play an important role in the assembly and adhesive functions of hemidesmosomes.

Various efforts have focused on purifying adhesion-facilitating proteins found in basement membranes. For example, Burgeson, et al., Patent Cooperation Treaty Application Nos. WO92/17498 and WO94/05316, disclose a protein which they call kalinin. Kalinin is said to facilitate cell adhesion to substrates; however, this material is apparently inactive with respect to hemidesmosome formation. See also, Marinkovich, et al., *J. Cell Biol.* 119:695–703, 1992 (k-laminin); Rouselle, et al., *J. Cell. Biol.,* 114:567–576, 1991 (kalinin); and Marinkovich, et al., *J. Biol. Chem.,* 267:17900–17906, 1992 (kalinin).

Similarly, a basement glycoprotein of about 600 kD comprising polypeptides in the range of 93.5 kD to 150 kD has been identified, and is known as GB3 or nicein. See, e.g., Verrando, et al., *Biochim. Biophys. Acta*, 942:45–56, 1988; and Hsi, et al., *Placenta*, 8:209–217, 1987. None of these materials has been effective in generating formation of hemidesmosomes, either in vitro or in vivo.

When cultured on tissue culture plastic in vitro, most epithelial cells do not assemble bona fide hemidesmosomes despite the fact that they appear to express all of the hemidesmosomal plaque and transmembrane components mentioned above. Indeed, only recently have cell lines such as 804G been discovered to have the ability to readily assemble hemidesmosomes in vitro under regular culture conditions (Riddelle, et al., *J. Cell Biol.*, 112:159–168, 1991; Hieda, et al., *J. Cell Biol.*, 116:1497–1506, 1992). Such cells are at last allowing detailed cell and biochemical analysis of the dynamics of hemidesmosome assembly.

For instance, it has been reported that substratum-associated staining by anti-hemidesmosome antibodies is greatly diminished in 804G cell cultures that enter in vitro wound sites (Riddelle et al., *J. Cell Sci.*, 103:475–490, 1992). However, as closure of the wound became complete, anti-hemidesmosome staining along the substratum-attached surface was evident in the cells.

There are, however, many epithelial cells that do not attach to tissue culture dishes in a normal fashion, even after treatment with various growth factors. These cells do not produce normal hemidesmosomes or grow to resemble their in vivo phenotype. It would provide a tremendous advantage to have a system that was capable of maintaining epithelial cell growth in vitro wherein the cells maintained their normal phenotype.

SUMMARY OF THE INVENTION

One embodiment of the present invention is a method for inducing hemidesmosome formation in epithelial cells, comprising the step of:

culturing epithelial cells unable to themselves form hemidesmosomes in the presence of an effective, hemidesmosome-formation facilitating amount of a soluble protein, wherein said soluble protein comprises one or more protein chains characterized as:

(a) soluble in aqueous medium;

(b) being bound by polyclonal antibodies present in serum of rabbits inoculated with the matrix secreted by 804G or NBT-II cells;

(c) being bound by monoclonal antibodies generated against the matrix secreted by 804G or NBT-II cells;

(d) promoting rapid epithelial cell adhesion to substrates coated with at least one of said protein chains; and (e) promoting hemidesmosome formation in epithelial cells.

Preferably, the protein chains have molecular weights of about 80 kD, 98 kD, 139 kD (β), 146 kD (γ) or 154 kD (α) as determined by SDS-polyacrylamide gel electrophoresis on a 6% gel in comparison to known molecular weight standards. The 154 kD (α) protein advantageously includes the sequence shown in SEQ ID NO: 1. Preferably, the soluble protein is obtained from 804G or NBT-II rat bladder carcinoma cells. Further, the protein chains may bind concanavalin. In another aspect of this embodiment, the soluble protein material is produced from recombinant DNA. The recombinant DNA may be of human, murine or other mammalian origin or a combination thereof. According to another aspect of this preferred embodiment, the 804G cells are adapted to grow in a low serum or serum-free medium.

In another aspect of this embodiment, the epithelial cells are human. Further, the soluble protein may be provided to the cells in a cell-free conditioned medium. Advantageously, the soluble protein is provided to the cells in a low serum or serum-free medium. Preferably, the soluble protein is capable of being immunopurified from 804G cell conditioned medium using at least one of the monoclonal antibodies. In addition, the soluble protein may be deposited on or in a shaped article.

The present invention also provides a method for facilitating growth of epithelial cells, comprising the steps of:

providing an effective cell growth-facilitating amount of a soluble protein comprising protein chains characterized as:

(a) soluble in aqueous medium;

(b) being bound by polyclonal antibodies present in serum of rabbits inoculated with the matrix secreted by 804G or NBT-II cells;

(c) being bound by monoclonal antibodies generated against the matrix secreted by 804G or NBT-II cells;

(d) promoting rapid epithelial cell adhesion to substrates coated with at least one of said protein chains; and (e) promoting hemidesmosome formation in certain epithelial cells capable of producing hemidesmosomes; and (f) contacting epithelial cells that are not producing effective amounts of said protein with an amount of said protein effective to facilitate increased growth of said epithelial cells.

Preferably, the epithelial cells are mammalian; most preferably human, and the soluble protein material is secreted by 804G or NBT-II cells. Further, the protein chains may bind concanavalin. Advantageously, the protein chains have molecular weights of about 80 kD, 98 kD, 139 kD (β), 146 kD (γ) and 154 kD (α) as determined by SDS-polyacrylamide gel electrophoresis on a 6% gel in comparison to known molecular weight standards. Preferably, the soluble protein is produced from recombinant DNA. The recombinant DNA may be of human, murine or other mammalian origin or a combination thereof.

Another embodiment of the invention is an 804G cell line that has been adapted to grow in a low serum or serum-free medium, such that the cell line secretes a soluble hemidesmosome formation-inducing protein into the culture medium.

Still another embodiment of the invention is the active hemidesmosome-inducing soluble protein that is produced by the cell line 804G, in substantially isolated or purified form. In another aspect of this preferred embodiment, the soluble protein is provided in a pharmaceutically acceptable carrier.

The present invention also provides a composition for use in growing mammalian cells comprising media preconditioned by growth of 804G cells, the media having the property of promoting hemidesmosome formation in cells contacting the media. Preferably, the media is a low serum or serum-free media and the cells are epithelial cells.

Another embodiment of the present invention is an article of manufacture, comprising:

a shaped article; and an effective cell growth-facilitating or hemidesmosome formation-facilitating amount of a soluble protein deposited on said shaped article, said protein comprising one or more protein chains characterized as:

(a) soluble in aqueous medium;

(b) being bound by polyclonal antibodies present in serum of rabbits inoculated with the matrix secreted by 804G or NBT-II cells;

(c) being bound by monoclonal antibodies generated against the matrix secreted by 804G or NBT-II cells;

(d) promoting rapid epithelial cell adhesion to substrates coated with said protein chain or chains; and (e) promoting hemidesmosome formation in epithelial cells.

Preferably, the protein chains have molecular weights of about 80 kD, 98 kD, 139 kD ($\beta$), 146 kD ($\gamma$) and 154 kD ($\alpha$) as determined by SDS-polyacrylamide gel electrophoresis on a 6% gel in comparison to known molecular weight standards. In an alternative embodiment, the article further comprises epithelial cells deposited on the deposited protein. Advantageously, the article is used in vivo. The article may be made of or coated with a biocompatible metal, a ceramic material or a polymer. Preferably, the protein chains bind concanavalin.

DETAILED DESCRIPTION

Figure 1:
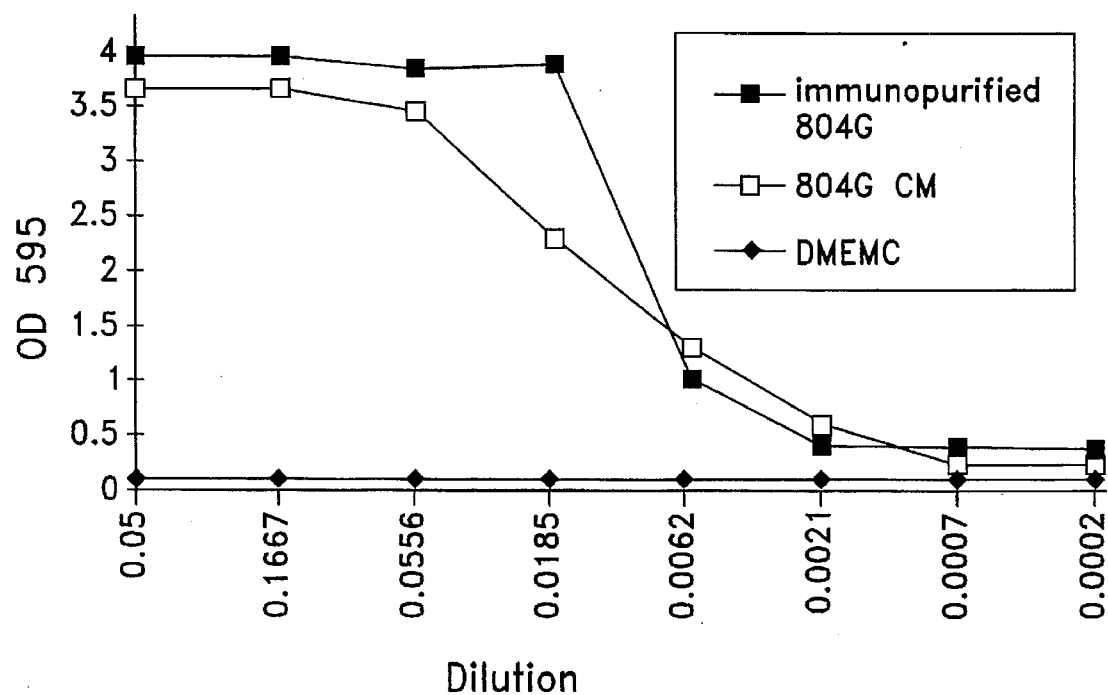
FIG. 1 is a graph illustrating the rapid adhesion of FGmet2 human pancreatic carcinoma cells to both 804G conditioned medium and TR1-immunopurified 804G soluble protein. The dilution of substrate is shown on the x-axis and the optical density at 595 nm (OD 595) is shown on the y-axis.

The present invention includes the discovery that a soluble protein secreted into the growth media by certain cell lines can stimulate cellular adhesion and hemidesmosome assembly in epithelial cells capable of producing hemidesmosomes plated thereon. This 804G soluble protein, termed secreted laminin due to its sequence homology to known laminins, promotes the formation of hemidesmosomes and/or rapid cell adhesion in some epithelial cells unable to themselves form hemidesmosomes. One type of cell having this ability is the rat bladder carcinoma cell line 804G. This cell line has been described by Izumi, et al. (*Cancer Res.*, 41:405–409, 1981), and is maintained as a Budapest Treaty patent deposit by the American Type Culture Collection (ATCC) 12301 Parklawn Drive, Rockville, Md., under accession number ATCC CRL 11555 made Feb. 24, 1994.

Secreted laminin contains three glycosylated protein chains having molecular weights of about 139 ($\beta$), 146 ($\gamma$) and 154 kD ($\alpha$) and is recognized by both polyclonal and monoclonal antibodies generated against the cellular matrix deposited by 804G cells. Secreted laminin may be purified by immunoaffinity chromatography using either these polyclonal or monoclonal antibodies. In addition, the generation of monoclonal antibodies using combinatorial libraries is also contemplated. The 804G soluble protein promotes rapid adhesion of epithelial cells to substrates coated with at least one of the protein chains.

The 804G secreted laminin may be purified in a number of ways. In a preferred embodiment, the protein is purified from 804G conditioned medium by immunoaffinity chromatography using a monoclonal antibody directed against any of its three protein chains. Purification of secreted laminin may be facilitated by culturing the cells under low serum or serum-free conditions which virtually eliminates contaminating proteases, protease precursors and other serum proteins. The protein may be purified from the conditioned medium, for example, by immunoaffinity chromatography or ammonium sulfate fractionation. Although the 804G cells were cultured in Dulbecco's Modified Eagles Medium:OPTI-MEM (1:1) in the presence of 1% fetal calf serum, the use of other media and other concentrations of fetal calf serum, preferably from about 0% to about 5%, is also within the scope of the present invention.

Ultrastructural data have demonstrated that the 804G secreted laminin can induce a number of different cell types to assemble mature hemidesmosomes and attach to their growth substrate. A solution can now be prepared, containing secreted laminin secreted by cells such as 804G cells, that can modulate the organization of hemidesmosomal antigens in unrelated cells. This effect appears specific to hemidesmosomal elements since adhesion plaque components do not obviously change their localization in cells contacted with the 804G secreted laminin.

To demonstrate our new discovery, we provide evidence that the murine secreted laminin is capable of inducing assembly of "mature" hemidesmosomes in the HaCaT immortalized human keratinocyte cell line. It can be appreciated that it is uncommon to find proteins from murine cells that have such a profound effect on human tissue. In the experiments described in more detail below, an increased number of hemidesmosome-like structures were found in HaCaT cells contacted with 804G growth media, as compared to control experiments wherein HaCaT cells were grown on rat tail collagen. Moreover, the majority of hemidesmosome-like structures in the treated cells contacted the cell-substrate and possessed basal dense plates. The basal dense plate structures are often used as indicators of mature or formed hemidesmosomes (Krawczyket al., *J. Ulrastruct. Res.*, 45:93–101, 1973).

The monoclonal antibody TR1 used for immunopurification of the 804G secreted laminin was generated against the cell matrix deposited by 804G cells by standard methods. Five other monoclonal antibodies directed to the 804G cell matrix, namely 5C5, BH5, CM6, DF2, and FM3, were also generated. These six antibodies, and the hybridoma cell lines from which they are derived, are maintained in the laboratory of Dr. Vito Quaranta, The Scripps Research Institute, La Jolla, Calif. These antibodies other than 5C5 precipitate the active soluble protein from 804G conditioned medium, but will not precipitate the related secreted laminin from SCC-25 human squamous carcinoma cells (ATCC CRL 1628). The use of any of these monoclonal antibodies in the immunopurification of secreted laminin is within the scope of the present invention, as is any monoclonal antibody capable of binding any of the secreted laminin protein chains.

Sodium dodecyl sulfate-polyacrylamide gel electrophoresis (SDS-PAGE) under reducing conditions dissociates the holoprotein into three protein chains of molecular weights 154 kD ($\alpha$), 146 kD ($\gamma$) and 139 kD ($\beta$). A 98 kD fragment and an 80 kD fragment related to the $\gamma$ subunit are also observed. The skilled artisan will appreciate that the molecular weight values of these secreted laminin protein chains will vary depending on the analytical technique employed. The molecular weight values were obtained using a 6% Tris-glycine precast SDS-polyacrylamide gel and Mark 12™ molecular weight standards from Novex, Inc. (San Diego, Calif.).

The 5C5 and CM6 antibodies bind to the $\beta$ subunit and the TR1, DF2, FM3 and DH5 antibodies bind to the $\beta$ subunit. Thus, the 804G secreted laminin is a heterotrimer comprising $\alpha$, $\beta$ and $\gamma$ chains. The intact purified protein may also be purified by ammonium sulfate fractionation or other well known purification methods.

Accordingly, TR1, or any other monoclonal antibody capable of recognizing any of the protein chains discussed above, can be used to immunopurify secreted laminin from any desired cell line or tissue. For example, human cell lines may be screened for production of secreted laminins by passage of the conditioned medium over a TR1 immunoaffinity column and analysis of the eluted proteins by both SDS-PAGE to determine molecular weight as described in Example 3, and by an assay to assess the ability of the eluted proteins to support rapid epithelial cell adhesion as described in Example 5.

The TR1-immunopurified protein promotes the rapid adhesion of FGmet2 human pancreatic carcinoma cells (Kajiji et al., *Cancer Res.*, 47:1367–1376, 1987), an epithelioid cell line, to plastic non-tissue culture treated multititer plates. The activity of the immunopurified protein in promoting rapid cell adhesion is significantly higher than the corresponding 804G conditioned medium from which the protein is purified. This may indicate a higher concentration of protein in the immunopurified preparation and/or the removal of proteases, protease precursors or other inhibitory proteins from the 804G conditioned medium by the chromatographic step.

Although methods relating to the production and isolation of 804G soluble protein are disclosed, it can be appreciated that any cell which secretes one or more proteins capable of supporting cell adhesion and/or hemidesmosome assembly in vitro is within the scope of the present invention.

Soluble proteins from other cell types are also capable of inducing epithelial cell attachment and hemidesmosome assembly in vitro. For example, culture supernatants from the murine bladder carcinoma cell line NBT-II (ATCC CRL 1655) induced hemidesmosome formation in vitro to a similar density compared to 804G culture supernatants. Further, culture supernatants from NBT-II cells promoted rapid cell adhesion of epithelial cells. In addition, proteins of identical molecular weights were immunprecipitated from both NBT-II and 804G culture supernatants by the J18 polyclonal antibody described in Example 2. The antibody reactivity pattern of the majority of the monoclonal antibodies mentioned above to the matrix deposited by 804G cells is identical between the 804G and NBT-II secreted laminins. The 804G matrix is described in U.S. Pat. No. 5,541,106, the entire contents of which are hereby incorporated by reference. The NBT-II cell line is also maintained as an ATCC Budapest Treaty patent deposit, deposited Feb. 24, 1994, and assigned accession number ATCC 11556. It should be noted that the term "804G soluble protein", equivalent to secreted laminin, is used herein to generically refer to any secreted cellular protein capable of stimulating cell attachment and/or hemidesmosome formation in at least some epithelial cell types.

The 804G soluble protein of the present invention comprises three concanavalin-binding glycoprotein chains, of approximately 139 kD ($\beta$), 146 kD ($\gamma$) and 154 kD ($\alpha$), and 98 kD and 80 kD non-glycosylated fragments related to the 146 kD ($\gamma$) protein, all of which are recognized by both polyclonal and monoclonat antibodies raised against the matrix deposited by 804G cells. These are the same protein components present in the 804G matrix. The present invention may be practiced with the entire secreted laminin protein or with at least one of the individual protein chains thereof capable of promoting cell attachment and hemidesmosome formation. The present invention may also be practiced with a functionally equivalent protein from other cell types.

As described in Example 10, the 140 kD and 150 kD proteins of the matrix deposited by 804G cells have been partially sequenced. These proteins correspond to the 146 kD ($\gamma$) and 154 kD ($\alpha$) chains of secreted laminin, respectively. The 5C5 and CM6 monoclonal antibodies recognize both the 150 kD matrix protein and the 154 kD ($\alpha$) chain of soluble secreted laminin, confirming the identity of these proteins. In addition, a polyclonal antibody, J20, directed against a peptide sequence contained within the 140 kD matrix protein also recognizes the 146 kD ($\gamma$) chain of secreted laminin.

Accordingly, oligonucleotide probes complementary to portions of these sequences may be used to probe any desired cDNA library using standard molecular biology techniques to identify related sequences from other cells and tissues within the same species or to identify related sequences from different species.

One major use contemplated for the 804G soluble protein or active fragments thereof is in cell growth and attachment. A substrate upon which cells are to be grown is coated with a solution comprising secreted laminin or an active fragment thereof. A desired cell type is then plated on or applied to the substrate. Such cells, including human cells both in vitro and in vivo, will rapidly adhere to the substrate, form hemidesmosomes and grow in an organized fashion. Hemidesmosome formation is a major advantage, because it greatly enhances the attachment of the cells to the substrate. Furthermore, it appears that the organization of cells plated on secreted laminin is significantly more advanced and more tissue-like than cells grown in the absence of secreted laminin.

The substrate used herein may be any desired substrate. For laboratory use, the substrate may be as simple as glass or plastic. For use in vivo, the substrate may be any biologically compatible material on which cells can grow. Suitable substrate materials may include shaped articles made of or coated with such materials as polyglycolic acid and polylactic acid; biocompatible metals such as stainless steel and titanium; ceramic materials including prosthetic materials such as hydroxylapatite; synthetic polymers including polyesters, nylons and polytetrafluoroethylene (PTFE); and virtually any other material to which biological molecules can readily adhere.

One particular use of the present invention is to increase epidermal cell adhesion to target surfaces. For instance, prostheses for dental implantation may be coated with secreted laminin to stimulate periodontal cell attachment. Existing teeth may similarly be coated as a treatment for gum (junctional epithelium) disease, such as gingivitis. Where a substrate is made of polymers of natural or synthetic bioerodible material in the form of a sheet or fabric, such as woven or bonded collagen, polylactic acid, lactide, glycolide, glutamic acid, collagen, or albumin, the soluble protein, chains or fragments thereof may be applied to the substrate surface or mixed in with the composition. Cells (such as epidermal cells) may then be grown on the deposited active laminin ex vivo to form transplantable or implantable materials; alternatively, the materials may be implanted and cells may be permitted to attach in vivo.

Secreted laminin will also be of great use in studies concerning hemidesmosome morphogenesis and $\alpha_6\beta_4$ integrin interactions with the epithelial extracellular matrix. Indeed, secreted laminin may allow definition of hemidesmosome-mediated interactions between epithelial cells and their underlying connective tissue at the molecular level.

In addition to secreted laminin and the active components thereof, the present invention also includes shaped articles coated with these materials. Preferably, these shaped articles are formed of materials other than glass, and include such forms as sheets, fabrics, prostheses, metal articles, bioerodible articles, and implantable articles.

Furthermore, pharmaceutical preparations containing secreted laminin or active fragments thereof are also contemplated. These preparations can be in any suitable form, and generally comprise the active ingredient in combination with any of the well known pharmaceutically acceptable carriers. The inclusion of one or more growth factors in these pharmaceutical preparations is also contemplated, as these factors will stimulate growth of the cells which adhere to the secreted laminin. Secreted laminin may be isolated from the growth media in which appropriate cells have been grown. Alternatively, the soluble factor may be prepared synthetically or through recombinant DNA techniques, or through purification of isolated proteins from the growth media.

Carriers can include injectable carriers, topical carriers, transdermal carriers, and the like. The preparation may advantageously be in a form for topical administration, such as an ointment, gel, cream, spray, dispersion, suspension, or paste. The preparations may further advantageously include preservatives, antibacterials, antifungals, antioxidants, osmotic agents, and similar materials in composition and quantity as is conventional. For assistance in formulating the compositions of the present invention, one may refer to Remington3 s Pharmaceutical Sciences, 15th Ed., Mack Publishing Co., Easton Pa. (1975), the relevant disclosure of which is hereby incorporated by reference.

Finally, epithelial cells of various types may be grown in contact with the compositions contemplated herein.

As a first step in discovering the properties of the hemidesmosome formation-inducing 804G soluble factor, HaCaT cells were contacted with 804G conditioned medium as described below.

EXAMPLE 1

Treatment of HaCaT Cells with 804G Soluble Protein

The immortalized human keratinocyte cell line HaCaT, provided by Dr. Norbert Fusenig, Heidelberg, Germany (Boukamp, et al., *J. Cell Biol.* 106:761–771, 1988), was cultured in DMEM medium (Bio-Whittaker, Walkersville, Md.) supplemented with 10% fetal calf serum (FCS, Bio-Whittaker) and antibiotics. The HaCaT cell line has normal keratinization properties in vitro, is positive for involucrin, filaggrin, cytokeratins 1, 10, 5, 6, 14, 16/17, 7, 8 and 19 and is negative for vimentin. Thus it has characteristics very similar to primary keratinocytes.

The rat bladder carcinoma cell line, 804G, and the human embryonic fibroblast cell line WI-38 (ATCC CCL 75) were also cultured in DMEM medium containing the same supplements.

Culture supernatants of 804G cells were collected from cultures which were approximately 70% confluent and reached confluence over a 48 hour period. At the end of this time, 15 mls of supernatant was collected from a 75 $cm^2$ culture flask. Supernatants from HaCaT and WI-38 cells were collected in the same manner over a 48 hour period.

HaCaT cells plated on tissue culture plastic in normal medium attach, spread very slowly, and still appear rounded two hours after seeding. In contrast, however, when the cells were seeded in the culture supernatant (conditioned medium) of 804G cells they attached to the growth substratum and acquired a flattened morphology within 30 minutes. After 24 hours, cells seeded in normal medium formed epithelioid islands whereas cells seeded in supernatant from 804G cells exhibited a spread-out morphology and appeared to migrate so as to uniformly cover the growth substratum. The 804G culture supernatant effect was evident even if the cells were plated in a 1:1 dilution of the supernatant with normal medium. As a control, HaCaT cells were also plated in their own culture supernatant and in medium collected from cultures of WI-38 human fibroblasts. HaCaT cells plated in either their own medium or WI-38 medium did not exhibit the growth and morphology of those cells plated in 804G medium.

We then performed the following experiments to analyze the effect of the 804G culture supernatant on hemidesmosomal elements.

EXAMPLE 2

Analysis of Hemidesmosome Development After Treatment with 804G Culture Supernatants To study the effect of 804G culture supernatants on the distribution of $\alpha_6\beta_4$ integrins, HaCaT cells were grown on glass coverslips, fixed and immunolabeled for $\alpha_6$ and $\beta_4$ integrin subunits, hemidesmosomal components, or epithelial matrix elements.

HaCaT cells were grown for 24 hours on glass coverslips for immunofluorescence microscopy either in normal medium, medium conditioned for 48 hours with 804G cells, or in co-culture (1:1) with 804G cells. The cells were fixed for 5 minutes in −20° C. methanol, washed in PBS and immunolabeled with the following antibodies:

(1) AA3; a mouse monoclonal antibody to the human $\beta_4$ integrin subunit (Tamura, et al., *J. Cell Biol.* 1990; 111:1593–1604). This antibody specifically binds to human integrin molecules.

(2) GOH3; a rat monoclonal antibody to the $\alpha_6$ integrin subunit (AMAC, Westbrook, Me.). This antibody reacts with human and mouse, but not rat integrin molecules.

(3) 6844; a rabbit polyclonal antiserum to the cytoplasmic terminal 15 amino acids of the $\alpha_6$ integrin subunit.

(4) J18; a rabbit antiserum to the solubilized matrix of 804G cells (Langhofer, et al., (1993) *J. Cell Sci.*, 105:753–764).

(5) 5C5; a mouse monoclonal antibody the solubilized matrix of 804G cells.

(6) J17; a rabbit antiserum against the 180 kD hemidesmosomal protein (Riddelle, et al., (1992) *J. Cell Sci.*, 103:475–490).

(7) P1E1; a mouse monoclonal antibody to epiligrin (from Dr. William G. Carter, Fred Hutchinson Cancer Research Center, Seattle, Wash., Carter, et al. 1991).

(8) BM165; a mouse monoclonal antibody to kalinin (from Dr. Robert E. Burgeson, Oregon Health Sciences University, Portland, Oreg., Rouselle, et al., *J. Cell. Biol.* (1991); 114:567–576; Marinkovich, et al., *J. Biol. Chem.* (1992); 267:17900–17906).

(9) GB3; a mouse monoclonal antibody to human basement membranes (from Accurate Chemical and Scientific Corporation, Westbury, N.Y., Verrando, et al., (1987) *Exp. Cell Res.*, 170:116–128; Verrando, et al., (1988) *Biochim. Biophys. Acta.*, 942:45–56).

Fluorescein isothiocyanate (FITC) or tetramethylrhodamine isothiocyanate (TRITC) conjugated anti-mouse and anti-rabbit antibodies were purchased from Jackson Immunoresearch Laboratories Inc. (West Grove, Pa.). FITC or TRITC conjugated anti-rat antibodies were from Sigma Chemical Corporation (St. Louis, Mo.).

After single or double immunolabeling the cells were studied under a Zeiss Axiophot microscope equipped with epifluorescence and phase contrast optics. Photographs were taken with a Leitz Orthomat E automatic camera system and Kodak TMY 400 film at EI 800.

The visualization and photography of living cells was performed with a Zeiss Axiovert microscope equipped with phase contrast optics and the same camera system as above.

In cells grown in normal medium, the $\alpha_6$ and $\beta_4$ integrin subunits had a patchy, finely granular distribution most clearly visualized at the edges of cell islands. In cells grown in the 804G supernatant, the $\alpha_6$ and $\beta_4$ subunits were reorganized into coarsely granular or "Swiss-cheese" type patterns. The same patterns were reflected in immunolabeling with any of the antibodies against epithelial matrix elements (P1E1, GB3, BM165) and with the antibody against the 180 kD hemidesmosomal protein (J17).

EXAMPLE 3

Electrophoretic Analysis of the Culture Medium

Polypeptide samples from the culture medium and solubilized matrix from 804G and HaCaT cells were analyzed by SDS-polyacrylamide gel electrophoresis on a 6% resolving gel (Laemmli, 1974) with the NOVEX (Encinitas, Calif.) electrophoresis system. The separated polypeptides of culture medium, or purified rat laminin and fibronectin as controls (Telios Pharmaceuticals/GIBCO, Grand Island, N.Y.) were electrophoretically transferred to Immobilon-P membranes (Millipore, Bedford, Mass.) and processed for immunoblotting with J18 and 5C5 antibodies. As controls, the polypeptides were immunoblotted with rabbit antiserum against rat laminin or rat fibronectin (Telios Pharmaceuticals, San Diego, Calif.). The Vectastain ABC immunoperoxidase or alkaline phosphatase were used to detect binding. (Vector Laboratories, Burlingame, Calif.).

The J18 polyclonal antibody reacted with these polypeptides in immunoblotting experiments, but did not cross-react with laminin or fibronectin, two common extracellular matrix proteins. However, the 804G cell matrix and conditioned medium do contain fibronectin, but only trace amounts of laminin-related material.

The 804G secreted laminin was purified by immunoaffinity chromatography as described below.

EXAMPLE 4

Immunoaffinity Chromatography

Secreted laminin was purified from 804G conditioned medium by affinity chromatography using the monoclonal antibody TR1. The monoclonal antibody was immobilized on Affi-Gel 10 (Bio-Rad, Richmond, Calif.). Conditioned medium from 804G cells was applied to the column under isotonic and neutral pH conditions. The flow-through was discarded. The column was washed with phosphate-buffered saline (PBS) to elute unbound proteins, followed by solution of bound active protein with 50 mM diethylenamine, 50 mM sodium phosphate, 100 mM sodium chloride, pH 11.6. The eluted fractions were immediately neutralized to prevent soluble protein inactivation.

TR1-immunopurified 804G soluble protein was assayed for promotion of rapid cell adhesion as described in the following example.

EXAMPLE 5

Rapid Adhesion Assay

Serial dilutions of either TR1-immunopurified protein, conditioned medium from 804G cells, or control medium (DMEM) was used to coat 96-well microtiter plates. The coated plates were incubated overnight at 4° C., then treated with phosphate buffered saline (PBS) containing 1% bovine serum albumin to block nonspecific binding sites. FGmet2 human pancreatic carcinoma cells ($4\times10^5$ cells/well) were then added in binding buffer (25 mM HEPES, pH 7.55, 1% BSA in DMEM) and allowed to adhere for 30 minutes at 37° C. The wells were washed with PBS to remove nonadherent cells and the attached cells were fixed with 3% paraformaldehyde in PBS. The fixed cells were stained for 15 minutes with 0.5% crystal violet, washed extensively with water and solubilized in 1% SDS. Absorbance of the solubilized, stained samples was measured on a plate reader at 595 nm. The higher the absorbance (OD) value, the greater the number of adherent cells. As can be seen in FIG. 1, the most active preparation was the immunopurified 804G secreted laminin preparation. As expected, the 804G conditioned medium from which the protein was immunopurified also promoted rapid cell adhesion, although the immunopurified protein was significantly more active than the conditioned medium. This is evident by the fact that the absorbance value for cells plated on the immunopurified protein did not decline until the 0.0062 dilution, while the absorbance value of cells plated on the 804G conditioned medium sharply declined at the 0.0185 dilution (three times the concentration of the 0.0062 dilution). This supports the assertion that the cell adhesion-promoting activity is indeed due to secreted laminin.

The polypeptide components of the 804G soluble hemidesmosome formation-inducing protein can also be identified by fluorography of $^{35}$S metabolically labeled proteins as described below.

EXAMPLE 6

Metabolic Labeling of 804G Cells

Metabolic labeling with $^{35}$S-methionine was performed by first incubating the cells for 30 minutes in starving medium (MEM-medium without methionine, supplemented with 1% dialyzed FCS, L-glutamine and antibiotics, GIBCO, Grand Island, N.Y.), and then replacing the medium with 3 ml of fresh MEM without methionine, supplemented with 1% dialyzed FCS and 250 µCi S-methionine (Tran S-Label ICN Biomedicals Inc., Costa Mesa, Calif.) for 10 hours.

Gels with radioactively labeled polypeptides were processed for fluorography according to Bonner and Laskey (1974) and exposed to Hyperfilm (Amersham Corporation, Arlington Heights, Ill.).

The incorporation of $^{35}$S-methionine indicated that the polypeptides were synthesized by the cells and not simply deposited into the matrix from the culture medium. Moreover, the polypeptides can be visualized by immunoblotting with J18 and 5C5 antibodies, thus confirming their identity with the 804G matrix proteins. When HaCaT cells are grown in 804G cell culture supernatant, and their matrix is processed for immunoblotting with 5C5, two reactive polypeptides can be identified, indicating that the soluble immunoreactive material from 804G supernatant is able to bind to the matrix of HaCaT cells.

The effect of the soluble 804G cell components on HaCaT cells was also evident at the ultrastructural level. When HaCaT cells are grown on cell culture plastic in normal culture medium, they attach to their growth substratum by means of extracellular matrix contacts that resemble rudimentary hemidesmosomes. Alternatively, when the cells were grown in 804G cell supernatant, they formed adhesion complexes that are by morphological criteria mature hemidesmosomes.

EXAMPLE 7

Immunodepletion of 804G Supernatant with J18 Antibodies

When the cells were grown in 804G supernatant immunodepleted with J18 antibody, only occasional hemidesmosomes could be identified at the ventral plasma membrane. Immunodepletion of 804G supernatant was carried out by treating 1 ml of culture supernatant three consecutive times with the J18 antibody coupled to 50 µl protein A coupled to crosslinked dextran (SEPHAROSE®) beads (2 µg antiserum/10 µl packed beads, Sigma). As a control, 804G supernatant was also depleted with normal rabbit serum coupled to protein A SEPHAROSE®. The cells were fixed in modified Karnowsky fixative (1% paraformaldehyde, 0.1 M Nacacodylate, 1.75% glutaraldehyde, 2.5mMCaCl$_2$) and processed for electron microscopy by routine methods. Thin sections were cut perpendicular to the cell layer and studied at 75 kV in a Hitachi Hu-12A microscope. The specificity of this effect is verified by the fact that immunodepletion with normal rabbit serum does not affect the hemidesmosome inducing potential of 804G supernatant. These immunodepletion experiments indicate that the hemidesmosome formation-inducing soluble protein secreted by 804G cells is substantially the same as that contained in the 804G matrix.

To facilitate purification of secreted proteins, the 804G cell line was adapted to grow under low serum conditions as described in the following example.

EXAMPLE 8

Growth of 804G Cells in Low Serum or Serum-Free Medium 804G cells were gradually adapted to grow in 1:1 DMEM:OPTI-MEM (GIBCO, Grand Island, N.Y.) supplemented with 1% FCS, 2 mM glutamine, 100 µg/ml penicillin and 50 µg/ml streptomycin. The resulting 804G cell subpopulation was named 804GMH. According to the manufacturer, OPTI-MEM contains low amounts of transferrin and insulin, molecular weights 80 and 6 kD, respectively, but no other proteins. 804G cells were also grown in DMEM in the complete absence of serum. Both cells grown in low serum and cells grown in the absence of serum produce secreted laminin.

The virtual absence of serum proteins in the culture medium simplifies the purification of hemidesmosome-inducing soluble factors as described below.

EXAMPLE 9

Purification of Active Laminin From 804GMH Culture Medium

For the collection of serum-free culture supernatant, confluent 804GMH cells grown under low serum conditions were removed by incubation with 0.02% trypsin, washed once with DMEM containing 10% FCS and cultured in DMEM:OPTI-MEM with no added FCS at a split ratio of 1:6. Culture supernatant was collected when 804GMH cells had been confluent for 24 hours. The supernatant was centrifuged at 5,000×g for 10 minutes and stored at −20° C. until use. Secreted proteins were purified by precipitation with ammonium sulfate at saturation. Culture supernatant (1 liter) was cleared of particulate material by centrifugation at 10,000×g for 30 minutes and transferred to another container on ice. Ammonium sulfate was slowly added, with stirring, to 30% saturation. The supernatant was then left at 4° C. overnight to allow complete precipitation. The sample was centrifuged for 30 minutes at 10,000×g and ammonium sulfate was added to a final concentration of 40% saturation. After precipitation and centrifugation, the supernatant was discarded and the pellet resuspended in 1 ml PBS. The protein was dialyzed against PBS, the protein concentration estimated by absorbance at 280 nm, and an aliquot analyzed by SDS-PAGE. Bands of 240, 150 and 140 kD were observed.

Although the soluble factor was purified from low serum medium using the technique described above, it can be appreciated that the purification may be performed using a variety of steps. In a particularly preferred embodiment, the protein is purified from low serum medium in substantially the same way as described in Examples 4 and 5 for conditioned medium containing 10% serum.

Thus, we have demonstrated that soluble factors produced by 804G cells are able to induce attachment and hemidesmosome assembly in mammalian cells and that the purification of these proteins from the culture medium is greatly facilitated by growing the cells under low serum conditions.

EXAMPLE 10

Isolation of Clones Corresponding to Secreted Laminin Chains

A human keratinocyte λgt11 expression library was purchased from Clontech, Inc., Palo Alto, Calif. and screened with the 804G matrix polyclonal serum J18 according to Huynh et al., (DNA Cloning: A Practical Approach, Volume I, D. Glover, ed., IRL Press, Oxford, 1985). Antibodies absorbed by the fusion protein products of the two clones showed reactivity with the 140 kD and 100 kD molecular weight species in an 804G matrix preparation and a whole cell extract of SCC12 cells. The J18 serum was also used to screen a rat 804G expression library. Two independent clones from which antibodies to the 140 kD 100 kD polypeptide components were epitope-selected revealed over 85% identity with stretches of 94 residues in domain IV and 86 residues in domain I/II of a recently identified variant of the B2 chain of laminin that has been termed laminin B2t (Kallunki et al., J. Cell Biol., 119:679–695, 1992). The B2t variant is not contained in EHS laminin, and therefore represents a new subunit. In addition, five clones from which antibodies to the rat 150 kD component were epitope-selected were isolated.

To further characterize positive clones, plaque lifts of nitrocellulose-bound fusion proteins were used to epitope-select antibodies (Sambrook et al., Molecular Cloning: A Laboratory Manual, 2nd ed., Cold Spring Harbor Press, Cold Spring Harbor, N.Y., 1989). cDNA inserts were subcloned into M13 vectors and sequenced by the Sanger dideoxy chain termination method (Sanger et al., (1977) Proc. Natl. Acad. Sci. USA, 74:5463–5467). Sequence analyses were made using the GCG sequence analysis software package (University of Wisconsin Biotechnology Center, Madison, Wis.).

The partial nucleotide sequence of the 140 kD clone revealed that it encoded a region including amino acids 550–810 in domain I/II of human laminin B2t (SEQ ID NO: 1). This experiment illustrates the cross-reactivity of the matrix-associated polypeptides with the laminin B2t variant.

The 150 kD clone encoded regions exhibiting sequence similarity to the Drosophila laminin A chain (Garrison et al., (1991) *J. Biol. Chem.*, 266:22899–22904). The overall sequence identity between 294 amino acids of the rat 150 kD sequence (SEQ ID NO: 2) and amino acid residues 2365–2724 of the Drosophila laminin A chain (SEQ ID NO: 3) was 25%, a significant overlap considering the evolutionary difference between rat and Drosophila. SEQ ID NO: 2 also exhibited 21% identity to amino acids 1634–1970 of human merosin (SEQ ID NO: 4), a laminin A isoform. This laminin-like soluble adhesion- and hemidesmosome formation-inducing protein secreted by 804G cells thus comprises three protein chains having molecular weights of 154, 146 and 139 kD. The 139 kD laminin B2t-related protein, corresponding to the 140 kD 804G matrix protein, is termed the β subunit. The 154 kD Drosophila laminin A-related protein, corresponding to the 150 kD matrix protein, is termed the α0 subunit.

EXAMPLE 11

N-terminal Sequencing

Matrix deposited by 804G cells was solubilized and subjected to SDS-PAGE. The gel was transferred to a PVDF filter (Immobilon; Amersham) by conventional methods and the filter was stained with Coomassie Blue to visualize protein bands. Bands corresponding to the γ and β chains were excised from the filter and either digested with proteases followed by N-terminal sequencing of the resulting fragments or directly subjected to N-terminal sequencing by Edman degradation. Two internal peptide sequences related to the 154 kD (60) chain were determined: SEQ ID NO: 6) and (SEQ ID NO: 7). These peptides are about 90% homologous to specific regions of the sequence of human epiligrin determined by Ryan et al. (*J. Biol. Chem.*, 269:22779, 1994). In addition, the 6 N-terminal residues of the γ chain (Thr Ser Arg Arg Glu Val; amino acids 1–6 of SEQ ID NO: 1) and 16 residues of the β chain (SEQ ID NO: 5) were also determined.

It should be noted that the present invention is not limited to only those embodiments described in the Detailed Description. Any embodiment which retains the spirit of the present invention should be considered to be within its scope. However, the invention is only limited by the scope of the following claims.

---

We claim:

1. A method for inducing hemidesmosome formation in epithelial cells, comprising the step of:
contacting said epithelial cells, unable to themselves form hemidesmosomes, with an effective hemidesmosome formation inducing amount of a soluble protein, wherein said soluble protein comprises three main protein chains having molecular weights of about 139 kD, 146 kD, and 154 kD, respectively, as determined by SDS-polyacrylamide gel electrophoresis on a 6% gel in comparison with known molecular weight standards, and having properties including:

(a) being soluble in aqueous medium;
(b) being bound by polyclonal antibodies present in the serum of rabbits inoculated with an extracellular matrix deposited by 804G rat bladder carcinoma cells or NBT-II rat bladder carcinoma, cells,
(c) being bound by monoclonal antibodies generated against said extracellular matrix;
(d) promoting rapid epithelial cell adhesion to substrates coated with said three main protein chains; and
(e) promoting hemidesmosome formation in said epithelial cells.

2. The method of claim 1, wherein said 154 kD protein contains the sequence shown in SEQ ID NO: 2.

3. The method of claim 1, wherein said 146 kD protein contains the sequence shown in SEQ ID NO: 1.

4. The method of claim 1, wherein said soluble protein has been obtained from 804G rat bladder carcinoma cells.

5. The method of claim 1, wherein said soluble protein has been obtained from NBT-II rat bladder carcinoma cells.

6. The method of claim 1, wherein said three main protein chains bind concanavalin.

7. The method of claim 4, wherein said 804G rat bladder carcinoma cells have been adapted to grow in a low serum or serum-free medium.

8. The method of claim 1, wherein said epithelial cells are human.

9. The method of claim 1, wherein said contacting occurs in a cell-free conditioned medium.

10. The method of claim 1, wherein said contacting occurs in a low serum or serum-free medium.

11. The method of claim 1, wherein said soluble protein is immunopurified from 804G rat bladder carcinoma cell conditioned medium using at least one of said monoclonal antibodies.

12. The method of claim 1, wherein said protein is deposited on or in a shaped article and said contacting occurs on or in said article.

13. A method for facilitating growth of epithelial cells, comprising the steps of:

provided an effective epithelial cell growth-facilitating amount of a soluble protein, wherein said soluble protein comprises three main protein chains having molecular weights of about 139 kD, 146 kD, and 154 kD, respectively, as determined by SDS-polyacrylamide gel electrophoresis on a 6% gel in comparison with known molecular weight standards, and having properties including:

(a) being soluble in aqueous medium;

(b) being bound by polyclonal antibodies present in the serum of rabbits inoculated with an extracellular matrix deposited by 804G rat bladder carcinoma cells or NBT-II rat bladder carcinoma cells;

(c) being bound by too notional antibodies generated against said extracellular matrix;

(d) promoting rapid epithelial cell adhesion to substrates coated with said three main protein chains; and (e) promoting hemidesmosome formation in said epithelial cells; and contacting epithelial cells that are not producing effective epithelial cell growth-facilitating amounts of said soluble protein with an amount of said soluble protein effective to facilitate increased growth of said epithelial cells.

14. The method of claim 13, wherein said epithelial cells are human.

15. The method of claim 13, wherein said soluble protein is secreted by 804G rat bladder carcinoma cells.

16. The method of claim 13, wherein said soluble protein is secreted by NBT-II rat bladder carcinoma cells.

17. The method of claim 13, wherein said three main protein chains bind concanavalin.

18. The method of claim 13, wherein said soluble protein is immunopurified from 804G rat bladder carcinoma cell conditioned medium using at least one of said monoclonal antibodies.

19. An isolated soluble protein that induces hemidesmosome formation in epithelial cells normally unable to themselves form hemidesmosomes, said protein comprising three main protein chains having molecular weights of about 139 kD, 146 kD and 154 kD, respectively, as determined by SDS-polyacrylamide gel electrophoresis on a 6% gel in comparison to known molecular weight standards, said 146 kD protein containing amino acids 1–6 of SEQ ID NO: 1 within its amino acid sequence and said 139 kD protein containing the sequence shown in SEQ ID NO: 5 within its amino acid sequence, said three main protein chains having properties including:

(a) being soluble in aqueous medium;

(b) being bound by polyclonal antibodies present in serum of rabbits inoculated with an extracellular matrix deposited by 804G rat bladder carcinoma cells or NBT-II rat bladder carcinoma cells;

(c) being bound by monoclonal antibodies generated against said extracellular matrix;

(d) promoting rapid epithelial cell adhesion to substrates coated with said three main protein chains; and (e) being obtainable from 804G rat bladder carcinoma cells or NBT-II rat bladder carcinoma cells.

20. The protein of claim 19, in a pharmaceutically acceptable carrier.

21. The soluble protein of claim 19, wherein said soluble protein is secreted by 804G rat bladder carcinoma cells.

22. The soluble protein of claim 19, wherein said soluble protein is secreted by NBT-II rat bladder carcinoma cells.

* * * * *